United States Patent [19]

Szmuszkovicz et al.

[11] Patent Number: 4,598,088
[45] Date of Patent: Jul. 1, 1986

[54] 2-PYRROLYL-CYCLOALKYL-AMIDE ANALGESICS

[75] Inventors: Jacob Szmuszkovicz; John M. McCall; Lester J. Kaplan, all of Kalamazoo; Moses W. McMillan, Portage, all of Mich.

[73] Assignee: The Upjohn Company, Kalamazoo, Mich.

[21] Appl. No.: 738,637

[22] Filed: May 29, 1985

Related U.S. Application Data

[62] Division of Ser. No. 495,857, May 18, 1983, abandoned.

[51] Int. Cl.[4] .................... A61K 31/40; C07D 207/20
[52] U.S. Cl. .................................. 514/429; 514/409; 548/407; 548/565
[58] Field of Search ...................... 548/565; 514/429

[56] References Cited

U.S. PATENT DOCUMENTS

| | | | |
|---|---|---|---|
| 4,065,573 | 12/1977 | Lednicer | 260/465 G X |
| 4,098,904 | 7/1978 | Szmuszkovicz | 260/465 D X |
| 4,145,435 | 3/1979 | Szmuszkovicz | 548/335 X |
| 4,212,878 | 7/1980 | Lednicer et al. | 260/349 X |
| 4,359,476 | 11/1982 | Kaplan et al. | 546/230 X |
| 4,360,531 | 11/1982 | McMillan et al. | 546/231 X |
| 4,438,130 | 3/1984 | Kaplan | 548/407 X |
| 4,460,600 | 7/1984 | Kaplan et al. | 260/349 X |
| 4,466,977 | 8/1984 | McMillan et al. | 260/349 X |

Primary Examiner—Joseph Paul Brust
Attorney, Agent, or Firm—John T. Reynolds

[57] ABSTRACT

N-[2-(2,5-dihydro-1H-pyrrol-1-yl)cycloaliphatic)]benzeneacetamide and -benzamide compounds, e.g., (1α,2β)-(±)-3,4-dichloro-N-[2-(2,5-dihydro-1H-pyrrol-1-yl)cyclohexyl]-N-methylbenzeneacetamide, and salts thereof, have useful analgesic activity, low abuse or physical dependence liability properties. Processes for their preparation are disclosed. Pharmaceutical compositions containing such compounds and methods for their use are also disclosed.

11 Claims, No Drawings

2-PYRROLYL-CYCLOALKYL-AMIDE ANALGESICS

CROSS-REFERENCE

This is a division of application Ser. No. 495,857 filed May 18, 1983 now abandoned.

INTRODUCTION

This invention relates to N-[2-amino(unsubstituted and oxy-group-substituted-cycloaliphatic)]phenylacetamide and -benzamide compounds. More particularly, this invention provides some new N-[2-(2,5-dihydro-1H-pyrrol-1-yl)cycloaliphatic)]benzeneacetamide and -benzamide compounds which have useful analgesic activity and low abuse liability, or which are useful as chemical intermediates to such useful compounds. Processes for their preparation are disclosed. Pharmaceutical compositions and methods of use are also provided.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[2-(N',N'dimethylamino)cyclohexyl]-N-methyl-2-(4-bromophenyl)-acetamide and trans-N-methyl-N-[2-(1-pyrrolidinyl)cyclohexyl]-2-(3,4-dichlorophenyl)acetamide, which have potent analgesic activity; the preferred compounds thereof have, in addition, only low to moderate apparent physical dependence liability compared to morphine and methadone. That Szmuszkovicz '435 patent also describes some prior art patent and publication background that may be of interest herein also.

Also, Szmuszkovicz U.S. Pat. No. 4,098,904 discloses some cis- and trans-N-(2-aminocycloaliphatic)benzamide compounds, e.g., N-methyl-N-[2-aminocycloaliphatic]benzamide compounds, e.g., N-methyl-N-[2-(1-pyrrolidinyl)cyclohexyl]-3,4-dichlorobenzamide, which have potent analgesic activity, making them useful for relieving pain in warm blooded animals. That '904 patent also discloses background patents and publications which may be of interest herein.

Lednicer U.S. Pat. No. 4,212,878, discloses some N-[(1-amino-4-(mono- or di-oxygen-group-substituted)-cyclohexyl)methyl]benzeneacetamide derivatives, e.g., 2-(3,4-dichlorophenyl)-N-[[8-(1-pyrrolidinyl)-1,4-dioxaspiro[4.5]dec-8-yl]-methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclo-hexanone ketal compounds, e.g., 4-(m-hydroxyphenyl)-4-(dimethylamino)-cyclohexanone ethylene ketal and 4-(m-hydroxyphenyl)-4-(n-butylmethyl-amino)cyclohexanone ethylene ketal, which are useful for relieving pain in animals, some of which compounds exhibit narcotic antagonist activity.

McMillan et al. U.S. Pat. No. 4,360,531 discloses some N-[2-amino(oxy-group-substituted-cycloaliphatic)]phenylacetamide and benzamide compounds, e.g., trans-3,4-dichloro-N-methyl-N-[7-(1-pyrrolidinyl)-1,4-dioxaspiro[4.5]dec-8-yl]benzeneacetamide and the pharmacologically acceptable salts thereof which are useful as analgesic drug compounds.

Kaplan et al. U.S. Pat. No. 4,359,476 discloses some N-[2-amino(oxy or thio group)substituted-cycloaliphatic]phenylacetamide and benzamide compounds, having the oxy- or thio-group substituents on a cycloaliphatic ring carbon adjacent to either of the nitrogen bearing carbon atoms of the cycloaliphatic ring, e.g., cis or trans-4-bromo-N-[3-methoxy-2-(1-pyrrolidinyl)cyclohexyl]-N-methylbenzamide and cis and trans-3,4-dichloro-N-methyl-N-[7-(1-pyrrolidinyl)-1,4-dioxaspiro[4.5]dec-6-yl]benzeneacetamide, and salts thereof, useful as analgesic drug compounds.

OBJECTS OF THE INVENTION

It is an object of the invention to provide some new unsubstituted or N-[(oxy or thio group substituted)-N-[2-(2,5-dihydro-1H-pyrrol-1-yl)cycloaliphatic]benzeneacetamide and -benzamide compounds which are useful as analgesic compounds or as chemical intermediates to analgesic compounds.

It is a further object of this invention to provide some new compounds of the above type which have useful analgesic properties, and only low to moderate physical dependence liability compared to the high physical dependence liability of morphine and methadone.

Other objects, aspects, and advantages of this invention will become apparent from reading the remaining specification and claims which follow.

SUMMARY OF THE INVENTION

Briefly, this invention provides some new N-[2-(2,5-dihydro-1H-pyrrol-1-yl)cycloaliphatic]benzeneacetamide and -benzamide compounds which may or may not bear oxy- or thio group substituents on a cycloaliphatic ring carbon adjacent or not adjacent to the nitrogen bearing carbons of that cycloaliphatic ring, e.g., cis and trans-3,4-dichloro-N-methyl-N-[7-(2,5-dihydro-1H-pyrrol-1-yl)-1,4-dioxaspiro[4.5]dec-8-yl]benzeneacetamide, and salts thereof, which have useful ranges of analgesic properties while also having low apparent physical dependence liability, and which also, hopefully, have reduced dysphoria inducing properties. This invention also includes compounds of the above general type which may exhibit some analgesic activity of their own, but which are of more importance as chemical intermediates for the preparation of more advantageous analgesic drug compounds included herein or useful ratio isotopes of useful compounds for metabolism and other pharmacological or medical studies. This invention also includes pharmaceutical compositions containing these compounds as an active analgesic component and the method of inducing analgesic activity in an animal patient, including humans, by administering one of these new compounds in an amount effective and sufficient to induce analgesic activity, regardless of pain origin, e.g., traumatic pain, bone pain, cancer pain, post-surgical pain, homotopic pain, menstrual pain, headache, and the like. The invention also relates to new compounds in pharmaceutical dosage unit forms to be used, hopefully more advantageously, for the relief of pain in valuable animals and human patients suffering pain.

Based on information available to date with representative compounds of this invention, the trans compounds are preferred for analgesic purposes.

DETAILED DESCRIPTION OF THE INVENTION

More particularly, this invention provides some new compounds of Formula I below wherein p and n are each integers independently selected from the group 0, 1, 2, 3, 4, and 5 so that the resulting aliphatic ring of the Formula I compound has from 5 to 8 ring carbon atoms, inclusive, and the $R_1$ and $R_2$ bearing carbon atom is separated from, or adjacent to, one of the nitrogen bearing carbons of that cycloaliphatic ring.

In detail, the compounds of this invention are those of the formula I wherein p and n are each full number integers 0, 1, 2, 3, 4 or 5 so that the resulting cycloaliphatic ring has five to eight carbon atoms; the wavy line bond ($\sim$) between the nitrogen in the 2-position and the cycloaliphatic ring carbon indicates the bond can be either cis- or trans- with respect to each substituent of the cycloaliphatic ring;

q is 0 or 1;

X and Y are independently selected from the group consisting of hydrogen, a halogen having an atomic number of from 9 to 35, trifluoromethyl, nitro, $C_1$–$C_3$-alkyloxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino (—NHC(O)$R_4$), sulfonic acid (—SO$_3$H), $C_1$–$C_3$-alkanoyl, $C_3$–$C_6$-(allylic)-alkenyloxy, benzoyl;

R is hydrogen or $C_1$ to $C_3$-alkyl;

$R_1$, taken separately, is hydrogen, hydroxy, mercapto(—SH), GR$_3$ or OC(=O)R$_4$ and $R_2$, taken separately, is hydrogen; or $R_1$ is GR$_3$ and $R_2$ is GR$_3$; or $R_1$ and $R_2$, taken together, are selected from the group consisting of —ECH$_2$CH$_2$E—, —E—CH$_2$CH$_2$CH$_2$—E—, —ECH$_2$CH(CH$_3$)CH$_2$—E—, —ECH$_2$C(CH$_3$)$_2$CH$_2$—E—;

=E,

=N$\sim$OH, and

=N$\sim$OC(O)CH$_3$, wherein each E is bivalent sulfur or oxygen;

wherein each G is bivalent sulfur or oxygen;

$R_3$ is $C_1$ to $C_3$-alkyl; and $R_4$ is H, or $C_1$ to $C_2$-alkyl; and the acid addition salts thereof, particularly pharmaceutically acceptable salts thereof.

Thus, these N-[2-(2,5-dihydro-1H-pyrrol-1-yl)]-compounds are defined so that (if $R_1$ and $R_2$ are other than hydrogen) the oxy- or thio-group substituent ($R_1$, $R_2$), (if present), can be separated from the nitrogen bearing cycloaliphatic ring carbons by at least one methylene (—CH$_2$—) group, in which case the $R_1$, $R_2$ substituents will be in the 4-position of the cyclopentyl ring compounds, in the 4- or 5-position of cyclohexyl ring compounds (or a mixture of a compound wherein the $R_1$, $R_2$-substituent will be in the 4-position with a compound wherein the $R_1$, $R_2$-substituent will be in the 5-position), in the 4-, 5- or 6-positions of cycloheptyl ring compounds (or a mixture of such $R_1$, $R_2$ position isomers), or in the 4, 5, 6, or 7-position of cyclooctyl ring compounds or the p and n definitions can be selected, so that the $R_1$, $R_2$-oxy or thio-group substituent(s) can be bonded to a cycloaliphatic ring carbon atom which is adjacent to the ring carbon atom bearing either the amido-nitrogen or the amino-nitrogen of the compounds.

The compounds of formula (I) or their acid addition salts in their crystalline state may sometimes be isolated from their reaction mixtures as solvates, i.e., with a discrete quantity of solvent, e.g., water, ethyl acetate, methanol, methylene chloride and the like, associated physically, and thus not affecting the chemical entity per se.

It will be recognized by those skilled in the organic chemical art that the carbon atoms at positions 1 and 2 of the cycloaliphatic ring of structure (I) to which nitrogens are bonded are asymmetrically substituted. Likewise, for certain definitions of $R_1$ and $R_2$, the cycloaliphatic ring carbon atom to which $R_1$ and $R_2$ are bonded may also be asymmetrically substituted. Each of these three carbon atoms can independently possess an R or S-configuration and thus a compound of the formula (I) may have as many as $2^3$ or 8 stereoisomers which comprise four pairs of enantiomers; each enantiomeric pair is termed a racemate. See, for example, J. B. Hendrickson, D. J. Cram, and G. S. Hammond, Organic Chemistry, Third Edition, McGraw-Hill Book Company, New York, N.Y., 1970, pages 198–230, particularly pages 207, 208, 213, 215. Of the four racemates, two will have the nitrogen-containing groups at positions 1 and 2 of structure (I) in a trans orientation: that is, the groups will be on opposite sides of the plane of the cycloaliphatic ring; such compounds will be generally referred to in this specification as trans compounds and are meant to include both possible configurations of the third substituted ring carbon if it is asymmetrically substituted. The other two racemates will have the nitrogen-containing groups at positions 1 and 2 of structure (I) in a cis orientation: that is, the groups will be on the same side of the cycloaliphatic ring; such compounds will be generally referred to in this specification as cis compounds and are meant to include both possible configurations of the third substituted ring carbon atom if it is asymmetrically substituted. The four racemates of structure (I) compounds can each exist as a mixture of the two enantiomers or each enantiomer of each pair can be separated. Varying mixtures of enantiomers are also possible. When it is desired to specify for a structure (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972–1976)," a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of formula I compounds is indicated by: (1) the arbitrary designation of 1α for the orientation of the substituent on (asymmetric) carbon atom number one; (2) the designation 2α or 2β when the substituent on (asymmetric) carbon atom number two is on the same or opposite side of the plane of the cycloaliphatic ring, respectively, relative to said $C_1$ substituent; and (3) the designation xα or xβ when the substituent on (asymmetric) cycloaliphatic ring carbon atom number x is on the same or opposite side of the plane of the cycloaliphatic ring, respectively, relative to said $C_1$ substituent.

Two isomers which differ only in the stereochemistry at one asymmetric carbon atom of the cycloaliphatic ring are sometimes referred to herein as epimers.

If desired the formula I compounds of this invention can be resolved into their respective d- and l-optical isomers by methods known in the art. In this case, the optical resolution can be done by at least two different routes. The resulting agents by either route are any of the known resolving agents such as optically active camphorsulfonic acid, bis-o-toluoyltartaric acid, tartaric acid, and diacetyl tartaric acid which are commercially available and which are commonly used for resolution of amines (bases), as for example in Organic Synthesis, Coll. Vol. V., p. 932 (1973), resolution of R-(+) and S-(−)-α-phenylethylamine with (−)-tartaric acid.

By the first method for resolving the compounds of this invention, for example, one of the aminoamide compounds can be converted into its optically active diastereomeric salts by reaction with an optically active acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as hereinafter described in the examples to the desired acid addition salt.

By the second method, which in the case of some of these compounds is preferred, the formula I compounds can be made into their respective d- and l-isomers, by first resolving each cis- or trans-1,2-cycloaliphatic unsymmetrically substituted amino-alcohol or diamine into its respective d- or l-isomers by treatment with the resolving agent, crystallization, separation and regeneration of the respective d- and l-compounds, for example, trans-d-diamine, trans-l-diamine, or the cis-d-diamine and cis-l-diamine, and then reacting the respective resolved diamine starting material with the desired aracyl imidazole (III), the acyl halide (IV) or the acid (V) in the presence of a condensing agent to form the respective cis or trans-d- or l-compound of formula I, which can then be converted to any desired pharmaceutically acceptable acid addition salt by procedures exemplified hereinafter.

In the above formula I compounds, the halogens having atomic numbers of from 9 to 35 are fluorine, chlorine and bromine, the term "$C_1$ to $C_3$-alkyl" means methyl, ethyl, n-propyl and isopropyl. $C_1$ to $C_2$-alkyl means methyl or ethyl. $C_3$-$C_6$-(allylic)alkenyloxy means a 2-propen-1-yloxy group containing zero to 3 additional aliphatic carbon atoms.

A preferred subgroup of the $R_1$, $R_2$-unsubstituted formula I compounds are the formula I compounds where p is 1 to 3, n is 1 to 3 so that the cycloaliphatic ring has 5 to 7 ring carbons, R is $C_1$ to $C_3$-alkyl, $R_1$ and $R_2$ are each hydrogen, E is oxygen, q is 0 or 1 and at least one of X and Y is a halogen having an atomic number of from 9 to 35, in the 3- and/or 4-positions of the phenyl ring, and the pharmacologically acceptable salts thereof.

Examples of such compounds include the cis- and trans-isomers and enantiomers of:
4-Bromo-N-[2-(2,5-dihydro-1H-pyrrol-1-yl)cyclohexyl]benzamide,
3,4-Dichloro-N-methyl-N-[2-(2,5-dihydro-1H-pyrrol-1-yl)cyclopentyl]benzamide,
4-Fluoro-N-ethyl-N-[2-(2,5-dihydro-1H-pyrrol-1-yl)cycloheptyl]-benzeneacetamide,
4-Bromo-N-propyl-N-[2-(2,5-dihydro-1H-pyrrol-1-yl)cyclohexyl]benzeneacetamide,
3,4-Dichloro-N-[2-(2,5-dihydro-1H-pyrrol-1-yl)cyclohexyl]-N-methylbenzeneacetamide,
3,4-Dibromo-N-[2-(2,5-dihydro-1H-pyrrol-1-yl)cyclooctyl]-N-ethylbenzeneacetamide, and the like, and the pharmacologically acceptable salts thereof.

Another preferred subgroup of the $R_1$, $R_2$-unsubstituted formula I compounds are those wherein p is 1 to 3;
n is 1 to 3;
R is $C_1$ to $C_3$-alkyl;
$R_1$ and $R_2$ are each hydrogen;
X is trifluoromethyl in the 3- or 4-position;
Y is hydrogen;
q is 0 or 1;
E is oxygen; and
the pharmacologically acceptable salts thereof. A preferred example of this subgroup of compounds is:
N-methyl-N-[2-(2,5-dihydro-1H-pyrrol-1-yl)cyclohexyl]-4-trifluoromethylbenzamide, or a pharmacologically acceptable salt, such as its methanesulfonate salt.

A preferred subgroup of these formula I non-adjacently substituted compounds are those wherein p is 1 to 3, n is 1 to 3 and p and n are selected so that the cycloaliphatic ring has 5 to 7 ring carbons, q is 0 or 1, and at least one of X and Y is a halogen having an atomic number of from 9 to 35 in the 3- or 4-positions, or both of X and Y are such halogens in the 3- and 4-positions of the phenyl ring;
R is $C_1$ to $C_3$-alkyl;
$R_1$ and $R_2$ are taken together to form the ring group of —ECH$_2$CH$_2$E— and each E is oxygen, and the pharmacologically acceptable salts thereof. Examples of compounds of this group include the cis- and trans-isomers of:
3,4-dichloro-N-methyl-N-[8-(2,5-dihydro-1H-pyrrol-1-yl)-1,4-dioxaspiro[4.5]dec-7-yl]benzeneacetamide,
3,4-dichloro-N-methyl-N-[7-(2,5-dihydro-1H-pyrrol-1-yl)-1,4-dioxaspiro[4.5]dec-8-yl]benzeneacetamide,
4-bromo-N-methyl-N-[7-(2,5-dihydro-1H-pyrrol-1-yl)-1,4-dioxaspiro[4.5]dec-8-yl]benzeneacetamide,
3-fluoro-N-ethyl-N-[7-(2,5-dihydro-1H-pyrrol-1-yl)-1,4-dioxaspiro[4.5]dec-8-yl]benzeneacetamide,
3,4-dibromo-N-propyl-N-[7-(2,5-dihydro-1H-pyrrol-1-yl)-1,4-dioxaspiro[4.5]dec-8-yl]benzeneacetamide,
3,4-dichloro-N-methyl-N-[7-(2,5-dihydro-1H-pyrrol-1-yl)-1,4-dioxaspiro[4.4]-non-8-yl]benzeneacetamide,
3,4-dichloro-N-methyl-N-[7-(2,5-dihydro-1H-pyrrol-1-yl)-1,4-dioxaspiro[4.6]-undec-8-yl]benzeneacetamide,
3,4-dichloro-N-methyl-N-[8-(2,5-dihydro-1H-pyrrol-1-yl)-1,4-dioxaspiro[4.6]-undec-7-yl]benzeneacetamide,
3,4-dichloro-N-methyl-N-[9-(2,5-dihydro-1H-pyrrol-1-yl)-1,4-dioxaspiro[4.6]-undec-8-yl]benzeneacetamide,
and the corresponding benzamides, e.g.,
4-bromo-N-[7-(2,5-dihydro-1H-pyrrol-1-yl)-1,4-dioxaspiro[4.5]dec-8-yl]benzamide,
3,4-dichloro-N-methyl-N-[7-(2,5-dihydro-1H-pyrrol-1-yl)-1,4-dioxaspiro[4.5]dec-8-yl]benzamide,
3,4-dichloro-N-methyl-N-[7-(2,5-dihydro-1H-pyrrol-1-yl)-1,4-dioxaspiro[4.4]-non-8-yl]benzamide,
3,4-dichloro-N-methyl-N-[7-(2,5-dihydro-1H-pyrrol-1-yl)-1,4-dioxaspiro[4.6]-undec-8-yl]benzamide,
3,4-dichloro-N-methyl-N-[8-(2,5-dihydro-1H-pyrrol-1-yl)-1,4-dioxaspiro[4.6]-undec-7-yl]benzamide,
3,4-dichloro-N-methyl-N-[9-(2,5-dihydro-1H-pyrrol-1-yl)-1,4-dioxaspiro[4.6]-undec-8-yl]benzamide,
and the like, and the pharmacologically acceptable salts thereof.

Another preferred group of these non-adjacently $R_1$, $R_2$-substituted compounds of formula I are those wherein p is 1 to 3, n is 1 to 3, such that the cycloaliphatic ring has from 5 to 7 ring carbon atoms; q is 0 or 1; at least one of X and Y is a halogen having an atomic number of from 9 to 35 in the 3- or 4-position or both of X and Y are such halogens in the 3- and 4-positions of the phenyl ring; R is $C_1$ to $C_3$-alkyl; $R_1$ is —$OR_3$ and $R_3$ is $C_1$ to $C_3$-alkyl and $R_2$ is hydrogen; E is oxygen; and the pharmacologically acceptable salts thereof. Examples of such compounds include the cis- and trans-isomers of 4-bromo-N-[5-methoxy-2-(2,5-dihydro-1H-pyrrol-1-yl)cyclohexyl]benzamide, 3,4-dichloro-N-[4-methoxy-2-(2,5-dihydro-1H-pyrrol-1-yl)cyclohexyl]-N-methylbenzeneacetamide, 3,4-difluoro-N-[4-methoxy-2-(2,5-dihydro-1H-pyrrol-1-yl)cyclohexyl]-N-ethylbenzamide, 3,4-dibromo-N-[5-methoxy-2-(2,5-dihydro-1H-pyrrol-1-yl)cyclohexyl]-N-methylbenzeneacetamide, 3,4-dichloro-N-[4-propoxy-2-(2,5-dihydro-1H-pyrrol-1-yl)cyclopentyl]-N-methylbenzeneacetamide, 3,4-dichloro-N-[4-methoxy-2-(2,5-dihydro-1H-pyrrol-1-yl)cycloheptyl]-N-methylbenzamide, 3,4-dichloro-N-[5-ethoxy-2-(2,5-dihydro-1H-pyrrol-1-yl)cycloheptyl]-N-methylbenzeneacetamide, 3,4-dichloro-N-[6-methoxy-2-(2,5-dihydro-1H-pyrrol-1-yl)cycloheptyl]-N-methylbenzamide, and the pharmacologically acceptable salts thereof.

Examples of other non-adjacently $R_1$, $R_2$-substituted compounds within the scope of this inventiion include:

(a) compounds of formula I wherein p is 1 to 3, n is 1 to 3, such that the cycloaliphatic ring has 5 to 7 carbon atoms therein; q is 0 or 1; at least one of X and Y is a halogen having an atomic number of from 9 to 35 in the 3-, or 4-positions, or both of X and Y are such halogens in the 3- and 4-positions of the phenyl ring; R is hydrogen or $C_1$ to $C_3$-alkyl; $R_1$ and $R_2$ are taken together to represent =E; E is oxygen; and the pharmacologically acceptable salts thereof, examples of which are the cis- and trans-isomers of 3,4-dichloro-N-methyl-N-[4-oxo-2-(2,5-dihydro-1H-pyrrol-1-yl)cyclohexyl]benzeneacetamide, 4-bromo-N-[4-oxo-2-(2,5-dihydro-1H-pyrrol-1-yl)cyclohexyl]benzamide, 3,4-difluoro-N-ethyl-N-[2-(2,5-dihydro-1H-pyrrol-1-yl)-4-oxocyclohexyl]benzeneacetamide, 3,4-dichloro-N-propyl-N-[5-oxo-2-(2,5-dihydro-1H-pyrrol-1-yl)cyclohexyl]benzamide, 4-bromo-N-methyl-N-[2-(2,5-dihydro-1H-pyrrol-1-yl)-4-oxocyclohexyl]benzeneacetamide, 3,4-dichloro-N-methyl-N-[4-oxo-2-(2,5-dihydro-1H-pyrrol-1-yl)cyclopentyl]benzamide, 3,4-dichloro-N-methyl-N-[4-oxo-2-(2,5-dihydro-1H-pyrrol-1-yl)cycloheptyl]benzeneacetamide, 3,4-dichloro-N-methyl-N-[5-oxo-2-(2,5-dihydro-1H-pyrrol-1-yl)cycloheptyl]benzamide, 3,4-dichloro-N-methyl-N-[6-oxo-2-(2,5-dihydro-1H-pyrrol-1-yl)cycloheptyl]benzeneacetamide and the like, and the pharmacologically acceptable salts thereof.

(b) compounds of formula I wherein p is 1 to 3, n is 1 to 3, such that the cycloaliphatic ring has 5 to 7 carbon atoms; q is 0 or 1; at least one of X and Y is a halogen having an atomic number of from 9 to 35 in the 3- or 4-positions, or both X and Y are such halogens in the 3- and 4-positions of the phenyl ring; R is hydrogen or $C_1$ to $C_3$-alkyl; $R_1$ is —$OC(O)R_4$ and $R_4$ is hydrogen or $C_1$ to $C_2$-alkyl and $R_2$ is hydrogen; E is oxygen; and the pharmacologically acceptable salts thereof, examples of which are the cis- and trans-isomers of N-[4-acetyloxy-2-(2,5-dihydro-1H-pyrrol-1-yl)cyclohexyl]-3,4-dichloro-N-methylbenzeneacetamide, N-[5-acetyloxy-2-(2,5-dihydro-1H-pyrrol-1-yl)cyclohexyl]-4-bromobenzamide, N-[4-acetyloxy-2-(2,5-dihydro-1H-pyrrol-1-yl)cyclohexyl]-3,4-difluoro-N-ethylbenzeneacetamide, N-[4-acetyloxy-2-(2,5-dihydro-1H-pyrrol-1-yl)cyclohexyl]-3,4-dibromo-N-(n-propyl)benzamide, N-[4-acetyloxy-2-(2,5-dihydro-1H-pyrrol-1-yl)cyclopentyl]-3,4-dichloro-N-methylbenzeneacetamide, N-[4-acetyloxy-2-(2,5-dihydro-1H-pyrrol-1-yl)cycloheptyl]-3,4-dichloro-N-methylbenzamide, N-[5-acetyloxy-2-(2,5-dihydro-1H-pyrrol-1-yl)cycloheptyl]-3,4-dichloro-N-methylbenzeneacetamide, N-[6-acetyloxy-2-(2,5-dihydro-1H-pyrrol-1-yl)cycloheptyl]-3,4-dichloro-N-methylbenzamide, and the like, and the pharmacologically acceptable salts thereof.

A preferred subgroup of the adjacently $R_1$, $R_2$-substituted formula I compounds are those wherein p is 0, n is 2, 3, or 4, so that the cycloaliphatic ring has 5 to 7 ring carbons, q is 0 or 1, and at least one of X and Y is a halogen having an atomic number of from 9 to 35 in the 3- or 4-positions or both of X and Y are such halogens in the 3- and the 4-positions of the phenyl ring; R is hydrogen or $C_1$ to $C_3$-alkyl; $R_1$ and $R_2$ are taken together to represent —E—$CH_2CH_2$—E— and E is oxygen; and the pharmaceutically acceptable salts thereof. Examples of compounds of this group include the cis- and trans-isomers of:

3,4-difluoro-N-methyl-N-[7-(2,5-dihydro-1H-pyrrol-1-yl)-1,4-dioxaspiro[4.5]dec-6-yl]benzeneacetamide, 4-bromo-N-[7-(2,5-dihydro-1H-pyrrol-1-yl)-1,4-dioxaspiro[4.5]dec-6-yl]benzamide, 3,4-dibromo-N-ethyl-N-[7-(2,5-dihydro-1H-pyrrol-1-yl)-1,4-dioxaspiro[4.6]undec-6-yl]benzeneacetamide, 3-bromo-N-(n-propyl)-N-[7-(2,5-dihydro-1H-pyrrol-1-yl)-1,4-dioxaspiro[4.5]dec-6-yl]benzamide, 3,4-dichloro-N-methyl-N-[7-(2,5-dihydro-1H-pyrrol-1-yl)-1,4-dioxaspiro[4.6]undec-6-yl]benzeneacetamide, 4-bromo-N-[7-(2,5-dihydro-1H-pyrrol-1-yl)-1,4-dioxaspiro[4.4]non-6-yl]benzamide, 3,4-difluoro-N-[6-methoxy-2-(2,5-dihydro-1H-pyrrol-1-yl)cyclohexyl]-N-methylbenzamide, and the like, and the pharmacologically acceptable salts thereof.

Another preferred group of the adjacently $R_1$, $R_2$-substituted compounds of the formula I type are those wherein p is 0, n is 2, 3, or 4, so that the cycloaliphatic ring has 5 to 7 ring carbons, q is 0 or 1, and at least one of X and Y is a halogen having an atomic number of from 9 to 35 in the 3- or 4-positions or, both of X and Y are such halogens in the 3- or 4-positions of the phenyl ring;

R is hydrogen or $C_1$ to $C_3$-alkyl; $R_1$ is —$OC(O)R_4$ and $R_2$ is hydrogen, or $R_1$ and $R_2$ taken together represent —E—$CH_2CH_2$—E—; E is oxygen; and the pharmaceutically acceptable salts thereof. Examples of such compounds include:

3,4-difluoro-N-[7-(2,5-dihydro-1H-pyrrol-1-yl)-1,4-dioxaspiro[4.6]undec-6-yl]-N-methylbenzeneacetamide, 4-bromo-N-methyl-N-[[7-(2,5-dihydro-1H-pyrrol-1-yl)]-1,4-dioxaspiro[4.6]undec-6-yl]benzamide, N-[6-acetyloxy-2-(2,5-dihydro-1H-pyrrol-1-yl)cyclohexyl]-3,4-dichloro-N-(n-propyl)benzeneacetamide, N-[2-(2,5-dihydro-1H-pyrrol-1-yl)-6-propionyloxy)cyclohexyl]-4-fluorobenzamide, and the like, and their pharmacologically acceptable salts.

Another preferred subgroup of the adjacently $R_1$, $R_2$-substituted formula I compounds are those wherein p is 2, 3, or 4, n is 0, $R_1$ and $R_2$ are varied, as above, so that the oxy or thio group substituent is on the cycloaliphatic ring carbon atom adjacent the carbon atom bearing the basic amino nitrogen. Examples of such compounds include:

N-ethyl-4-fluoro-N-[2-(2,5-dihydro-1H-pyrrol-1-yl)-3-(propionyloxy)cyclohexyl]benzamide, 3,4-dibromo-N-propyl-N-[6-(2,5-dihydro-1H-pyrrol-1-yl)-1,4-dioxaspiro[4.6]undec-7-yl]benzeneacetamide, 4-bromo-N-[6-(2,5-dihydro-1H-pyrrol-1-yl)-1,4-dioxaspiro[4.5]dec-7-yl]benzamide, 3,4-dichloro-N-[[6-(2,5-dihydro-1H-pyrrol-1-yl]-1,4-dioxaspiro[4.5]dec-7-yl]-N-methylbenzeneacetamide, 4-bromo-N-[3-methoxy-2-(2,5-dihydro-1H-pyrrol-1-yl)cycloheptyl]-N-methylbenzamide, and the pharmacologically acceptable salts thereof.

Another preferred subgroup of compounds within the scope of this invention are those wherein p is 0, 1, 2, 3 or 4; n is 0, 1, 2, 3 or 4; q is 0 or 1; at least one of X and Y is a halogen having an atomic number of from 9 to 35 in the 3- or 4-positions, or both of X and Y are such halogens in the 3- and 4-positions of the phenyl ring; R is hydrogen or $C_1$ to $C_3$-alkyl; $R_1$ is $GR_3$ and $R_2$ is $GR_3$ and G is oxygen and $R_3$ is $C_1$ to $C_3$-alkyl; E is oxygen; and the pharmacologically acceptable salts thereof. Examples of such compounds include the cis- and trans-isomers of 3,4-dichloro-N-[4,4-dimethoxy-2-(2,5-dihydro-1H-pyrrol-1-yl)cyclohexyl]-N-methylbenzeneacetamide, 4-bromo-N-[4,4-dimethoxy-2-(2,5-dihydro-1H-pyrrol-1-yl)-cyclohexyl]-N-methylbenzamide, 3,4-dichloro-N-[6,6-dimethoxy-2-(2,5-dihydro-1H-pyrrol-1-yl)cyclohexyl]-N-methylbenzeneacetamide, 3,4-dibromo-N-[4,4-dimethoxy-2-(2,5-dihydro-1H-pyrrol-1-yl)cyclopentyl]-N-methylbenzeneacetamide, 3-chloro-N-[3,3-diethoxy-2-(2,5-dihydro-1H-pyrrol-1-yl)cycloheptyl]-N-methylbenzeneacetamide, 4-fluoro-N-[5,5-(di-n-propoxy)-2-(2,5-dihydro-1H-pyrrol-1-yl)cycloheptyl]benzamide, and the like and pharmacologically acceptable salts thereof.

Examples of 8-membered ring compounds within the scope of this invention include the cis- and trans-isomers of the following compounds:

3,4-dichloro-N-methyl-N-[2-(2,5-dihydro-1H-pyrrol-1-yl)cyclooctyl]benzeneacetamide, 4-bromo-N-[2-(2,5-dihydro-1H-pyrrol-1-yl)cyclooctyl]benzamide, 3,4-dichloro-N-[4-methoxy-2-(2,5-dihydro-1H-pyrrol-1-yl)cyclooctyl]-N-methylbenzeneacetamide, 4-bromo-N-methyl-N-[4-(methylthio)-2-(2,5-dihydro-1H-pyrrol-1-yl)cyclooctyl]benzamide, N-[3-methoxy-2-(2,5-dihydro-1H-pyrrol-1-yl)cyclooctyl]-4-methylbenzamide, 3,4-dichloro-N-methyl-N-[7-(2,5-dihydro-1H-pyrrol-1-yl)-1,4-dioxaspiro[4.7]dodec-8-yl]benzeneacetamide, N-methyl-3-nitro-N-[5-oxo-2-(2,5-dihydro-1H-pyrrol-1-yl)cyclooctyl]benzamide, 3,4-dibromo-N-[6,6-bis(methylthio)-2-(2,5-dihydro-1H-pyrrol-1-yl)cyclooctyl]-N-methylbenzeneacetamide, 4-chloro-N-[7-hydroxy-2-(2,5-dihydro-1H-pyrrol-1-yl)cyclooctyl]benzamide, 3-bromo-N-methyl-N-[7-(2,5-dihydro-1H-pyrrol-1-yl)-1,4-oxathiaspiro[4.7]dodec-6-yl]benzeneethanethioamide, and the like, and pharmacologically acceptable salts thereof.

In general, the new compounds of this invention (formula I compounds above) can be prepared by reacting the selected 1,2-cycloaliphatic diamine of the formula II, wherein p, n, R, $R_1$, and $R_2$, are as defined above with: (1) a suitable acyl source such as the appropriate acyl imidazole of the formula III

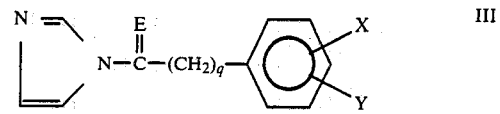

wherein q, E and Y are as defined above; (2) or with an acyl halide of the formula IV

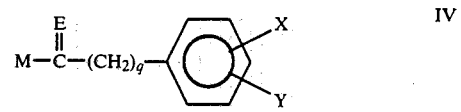

wherein M is chloride or bromide and q, E, X and Y are as defined above in the presence of an acid scavenger such as triethylamine; or (3) with the carboxylic acid of the formula V

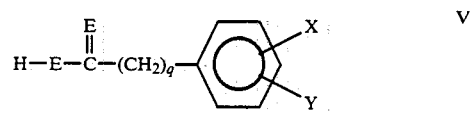

in the presence of a condensing agent, such as a carbodiimide, wherein q, E, X and Y are as defined above, in an organic solvent for the reactants, preferably in a chlorinated alkane, e.g., methylene chloride, ethylene dichloride, chloroform or carbon tetrachloride or in an ether solvent such as diethyl ether, or a cyclic ether solvent such as tetrahydrofuran (THF) or dioxane, or the like, until the compound of this invention is produced. Carbodiimides such as dicyclohexylcarbodiimide or diisopropylcarbodiimide can be used as condensing agents.

The reactants (II) and (III) or (II) and (IV) or (II) and (V) can be mixed in substantially equimolar proportions to effect formation of the desired product (I), but in cases where the non-pertinent amino nitrogens are protected against reaction, if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the formula (V) in an organic solvent. The carboxylic acids (V) are either known in the art or are prepared by methods known in the art.

Acid addition salts can be prepared by reacting a formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, furmaric, oxalic acids and the like. The reaction can be carried out in aqueous or organic liquid solvent or non-aqueous media such as diethyl ether, ethyl acetate, and the like. Non-aqueous media are preferred. When it is desired to obtain optically resolved products in crystalline form, it may be more convenient to form salts such as maleates, citrates or pamoates rather than the inorganic acid addition salts, such as the hydrochlorides. Also, whereas oxalic acid and other equivalent acids can be used to produce the amino-amide product in a more easily handled solid form, e.g., in plant manufacturing isolation procedures, it would preferably not be used as a pharmaceutically acceptable salt form of the amino-amide product.

In preparing the compounds of this invention the source of the 2,5-dihydro-1H-pyrrol-1-yl moiety is generally 2,5-dihydro-1H-pyrrole

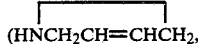
(HNCH$_2$CH=CHCH$_2$, also known as 3-pyrroline) which is known in the literature (Chemical Abstracts Registry Number 109-96-6) and is presently commercially available.

Procedures for preparing the diamine starting materials (II) have already been described in the U.S. patents and pending applications listed below, it being necessary only to substitute the 2,5-dihydro-1H-pyrrole for the amine groups listed for placement in the 2-position of the cycloalkyl rings of the diamines listed therein, recognizing that reaction conditions chosen should not unfavorably alter the double bond of the 2,5-dihydro-1H-pyrrole ring if present. Such patents and pending patent applications are
U.S. Pat. No. 4,145,435,
U.S. Pat. No. 4,098,904,
U.S. Pat. No. 4,360,531,
U.S. Pat. No. 4,359,476
and pending U.S. applications.

See West German published application No. P 32 41 933.3, published May 26, 1983 and Belgian Pat. No. 895,002, issued May 13, 1983.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combinations with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg per kg to about 5 mg per kg of body weight of the recipient. Preferred dosages for most applications are 0.05 to 2.0 mg per kg of body weight.

The useful pharmaceutical dosage unit forms of these compounds in pharmaceutical formulations are preferably adapted for systemic administration to obtain analgesic effects comprising an effective, non-toxic amount of a compound according to formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure analgesia and the physical dependence liability of the test compounds in standard laboratory test animals.

Representative examples of these formula I compounds have $ED_{50}$ values of less than about 75 mg/kg s.c. (subcutaneous administration) in standard laboratory animal analgesic tests such as the tail flick, pinch, and hydrochloric acid writhing tests, and the more potent of them have $ED_{50}$ values of less than 10 mg/kg (s.c.) in these tests, while at the same time possessing low apparent physical dependence liability as compared to commercial analgesics used as standards. The procedures used to determine these properties are essentially those of Way et al., (Way, E. L. et al., "Simultaneous Quantitative Assessment of Morphine Tolerance and Physical Dependence", J. Pharmacol. Exp. Ther., 167, pp. 1-8 (1969)) and Saalens et al., (Saalens, J. K. et al., "The Mouse Jumping Test—A Simple Screening Method to Estimate the Physical Dependence Capacity of Analgesics", Arch. Int. Pharmacodyn., 190, pp. 213-218 (1971)). Statistical effective doses ($ED_{50}$ values) and 95% confidence limits were calculated by the method of Spearman and Karber (Finney, D. J., "Statistical Methods in Biological Assay", Hafner Publ., (1952)).

Known analgesic drugs such as morphine and methadone exhibit analgesic $ED_{50}$ values of less than 2 mg/kg s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg/kg s.c.

Other representative compounds of this invention have analgesic potencies somewhat less than the preferred compounds (an analgesic activity $ED_{50}$ values up to about 75 mg/kg s.c., in these standard tests), and some such compounds still are characterized by having only low to moderate apparent physical dependence liability.

It has been found that a representative compound of this invention, $(1\alpha,2\beta)$-($\pm$)-3,4-dichloro-N-[2-(2,5-dihydro-1H-pyrrol-1-yl)cyclohexyl]-N-methylbenzeneacetamide (see Example 1 below) is surprisingly and unexpectedly more potent in these analgesic tail flick, pinch and writhing tests than the known compound, $(1\alpha,2\beta)$-($\pm$)-3,4-dichloro-N-methyl-N-[2-(1-pyrrolidinyl)cyclohelxyl]benzeneacetamide (the compound of Example 14 of U.S. Pat. No. 4,145,435, listed above). It has further been found that the (−)-enantiomer form (see Example 2 below) of this representative compound of this invention is more potent in these same analgesic tests than either the racemate form (Example 1 below) or the (+)-enantiomer form (see Example 3 below) of the same compound. Nevertheless the (+)-enantiomer form (Example 3 below) of this compound of this invention has surprising potency in these same analgesic tests.

The invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, IR (or ir) means infrared spectrum points of reference, m/e means the mass of a mass spectral fragment divided by its charge, M+ means the mass corresponding to the parent molecular ion, $CH_2Cl_2$ means methylene chloride solvent, dried ($K_2CO_3$) or dried ($Na_2SO_4$) or dried ($MgSO_4$) means the organic layer was dried over anhydrous forms of potassium carbonate, sodium sulfate, or magnesium sulfate, respectively, mp means melting point, NMR (or nmr) means nuclear magnetic resonance spectrum and NMR ($CDCl_3$) means a nuclear magnetic resonance spectrum made using deuteriochloroform as a solvent and values in parts per million are reported as downfield shifts from a tetramethylsilane internal reference; DBN means 1,5-diazabicyclo[4.3.0]-non-5-ene; h means hour(s), $N_2$ means nitrogen, tlc means thin layer chromatography procedures, $Na_2SO_3$ means sodium sulfite, $NaHCO_3$ means sodium bicarbonate, DMSO is dimethylsulfoxide, Skellysolve B (or Skelly B) is a tradename for a solvent of essentially n-hexane, bp 60°-68° C. (Merck Index, Ninth Edition (1976) page 1106), $Et_2O$ means diethyl ether, MeOH means methanol, THF means tetrahydrofuran, $H_2O$ means water, $CHCl_3$ means chloroform, brine is saturated aqueous sodium chloride solution, DMF means N,N-dimethylformamide, $Et_3N$ is triethylamine, HRMS means high resolution mass spectrum, EtOAc means ethyl acetate; HCl means hydrogen chloride.

EXAMPLE 1

$(1\alpha,2\beta)$-($\pm$)-3,4-Dichloro-N-[2-(2-,5-dihydro-1H-pyrrol-1-yl)cyclohexyl]-N-methylbenzeneacetamide and its maleate salt A. Preparation of $(1\alpha,2\beta)$-($\pm$)-2-(2,5-dihydro-1H-pyrrol-1-yl)-N-methylcyclohexanamine Cyclohexene epoxide (32.67 g., 0.333 mole) and 2,5-dihydro-1H-pyrrole (23.6 g., 0.333 mole) in 60 ml. of water are heated for 24 hours at 70° C. The mixture is partitioned between methylene chloride and water. The organic phase is dried over sodium sulfate and concentrated in vacuo. The residue is distilled (80°-90° C./0.4 mm. Hg.) (53.3 Pa units) to yield 43.36 g. of $(1\alpha,2\beta)$-2-(2,5-dihydro-1H-pyrrol-1-yl)cyclohexanol as an oily liquid. All of this is dissolved in 600 ml. of methylene chloride and stirred at 0° C. with 32 g. (0.31 mole) of triethylamine. Methanesulfonyl chloride (35.51 g., 0.31 mole) is added and the mixture is stirred for 35 min. at 0° C. The solution is partitioned with ice water. The organic phase is dried over sodium sulfate and concentrated in vacuo. The residue is transferred to a 1-liter Parr Pressure Reactor. A solution of 40% methylamine in water (150 ml.) is added and the mixture is heated at 70° C. for 20 hours. The mixture is then partitioned with diethyl ether and 10% aqueous sodium hydroxide. The ether layer is extracted with 1.2M HCl. The acidic aqueous layer is extracted with diethyl ether. The acidic aqueous layer is then made basic with 10% sodium hydroxide and extracted with diethyl ether. The ether layer is washed with brine and concentrated. The residue is dissolved in methylene chloride, dried over sodium sulfate, and concentrated in vacuo. The residue is distilled (80° C./0.3 mm. Hg.) (39.99 Pa units) to yield 39.0 g. of (1α,2β)-(±)-2-(2,5-dihydro-1H-pyrrol-1-yl)-N-methylcyclohexanamine.

B. (1α,2β)-(±)-3,4-Dichloro-N-[2-(2,5-dihydro-1H-pyrrol-1-yl)cyclohexyl]-N-methylbenzeneacetamide and its maleate salt A mixture of 4.41 g. (24.5 mmole) of the (1α,2β)-(±)-2-(2,5-dihydro-1H-pyrrol-1-yl)-N-methylcyclohexanamine from Part A above, 5.16 g. (31.8 mmole) of N,N'-carbonyldiimidazole and 6.52 g. (31.8 mmole) of 3,4-dichlorophenylacetic acid in 100 ml. of methylene chloride is stirred for 20 hours. The mixture is washed with aqueous sodium bicarbonate solution; the organic layer is dried over anhydrous sodium sulfate, filtered and concentrated in vacuo. The residue is chromatographed on silica gel eluting with 2% (10% concentrated ammonium hydroxide in methanol)-98% ethyl acetate to give 2.10 g of the titled amino-amide. This product is partitioned between methylene chloride and water, and the organic layer is dried over anhydrous sodium sulfate, filtered, and concentrated in vacuo. This titled amino-amide is converted to its maleate salt by reaction with an equivalent amount of maleic acid in diethyl ether solution to give, after evaporation and trituration with ethyl acetate, 1.83 g of the titled amino-amide maleate, mp 200°-202° C. The nmr and mass spectra support the titled amino-amide structure. This product has a C:H:N ratio of 57.21:-5.90:5.58; calculated for $C_{19}H_{24}N_2Cl_2O \cdot C_4H_4O_4$:57.14:-5.84:5.97.

Repetition of this experiment on a two-fold larger scale gives 7.98 g of the titled amino-amide after chromatography, and 7.58 g of the titled amino-amide after partitioning this material with aqueous sodium bicarbonate, drying over anhydrous sodium sulfate, filtering and concentrating in vacuo.

EXAMPLE 2

[1S-(1α,2β)]-(−)-3,4-dichloro-N-[2-(2,5-dihydro-1H-pyrrol-1-yl)-cyclohexyl]-N-methylbenzeneacetamide and its maleate salt A. Resolution of (1α,2β)-(±)-2-(2,5-dihydro-1H-pyrrol-1-yl)-N-methylcyclohexanamine. Preparation of (1α,2β)-(+)-2-(2,5-dihydro-1H-pyrrol-1-yl)-N-methylcyclohexanamine.

3.64 g (20.2 mmole) of the subtitled racemic amine and 7.81 g (20.2 mmole) of di-p-toluoyl-d-tartaric acid are each separately dissolved in a minimum volume of methanol, and the two solutions are mixed together. Crystallization starts very quickly. After 2 days of standing the mixture is filtered. There is obtained 8.00 g of a white crystalline solid (A). The solid is recrystallized from 300 ml of hot (60° C.) methanol to obtain 5.00 g of crystalline material (B), m.p. 186°-188° C. This crystalline material is recrystallized from 100 ml of methanol to obtain 3.27 g (C) of white crystalline material, m.p. 187°-188° C.

Small samples of crystalline materials (B) and (C) above are partitioned between ethyl acetate and 10% (w/v) sodium hydroxide aqueous solution. There is obtained 39 mg of crystalline material from sample B which was dissolved in 4.0 ml of methanol. The $[\alpha]\lambda^{25°}$ C. rotation constants for this sample are:

| λ | Hg 578 | 546 | 436 | 365 | Na 589 |
|---|---|---|---|---|---|
| $[\alpha]\lambda^{25°\ C.}$ | 114.8° | 129.8° | 216.1° | 328.6° | 110° |

From Sample C, there is obtained 21 mg of crystalline material which is dissolved in 2.0 ml of methanol. The $[\alpha]\lambda^{25°}$ C. rotation figures are:

| λ | Hg 578 | 546 | 436 | 365 | Na 589 |
|---|---|---|---|---|---|
| $[\alpha]\lambda^{25°\ C.}$ | 114.6° | 129.6° | 215.6° | 327.8° | 109.8° |

The remainder of the 3.27 g portion of the crystalline material (C) is partitioned between 10 percent w/v sodium hydroxide aqueous solution and ethyl acetate; the organic layer is washed twice with brine and is dried over sodium sulfate. The solvent is evaporated under vacuum, the residue is dissolved in methylene chloride, dried with sodium sulfate and the solvent is evaporated under vacuum to obtain 1.20 g. (D) of the (1α,2β)-(+)-2-(2,5-dihydro-1H-pyrrol-1-yl)-N-methylcyclohexanamine. A 39 mg. portion of this material (D) is dissolved in 4.0 ml of methanol and the $[\alpha]\lambda^{25°}$ C. rotation figures are measured as above.

| λ | Hg 578 | 546 | 436 | 365 | Na 589 |
|---|---|---|---|---|---|
| $[\alpha]\lambda^{25°\ C.}$ | +104.2° | +117.7 | +196 | +297.6° | +99.89° |

B. [1S-(1α,2β)]-(−)-3,4-Dichloro-N-methyl-N-[2-(2,5-dihydro-1H-pyrrol-1-yl)cyclohexyl]benzeneacetamide, and its maleate salt.

A mixture of 1.20 g (6.67 mmole) of the (+)-diamine from Part A above, 1.30 g (8.00 mmole) of N,N'-carbonyldiimidazole and 1.64 g of 3,4-dichlorophenylacetic acid in 25 ml of methylene chloride is stirred overnight and purified as described in Example 1, Part B above to give 1.30 g of the pure titled (−)-amino-amide. The Nuclear Magnetic Resonance spectrum of the product is in excellent agreement with this named compound. The $[\alpha]\lambda^{25°}$ C. rotation figures, obtained by dissolving a 14 mg sample of the product in 1.50 ml of methanol are:

| λ | Hg 578 | 546 | 436 | 365 | Na 589 |
|---|---|---|---|---|---|
| $[\alpha]\lambda^{25°\ C.}$ | −10.5° | −12.4° | −24.8° | −47.6° | −10.0° |

The maleate salt of this (−)-amino-amide compound is prepared by adding a mixture of 0.96 g of the above titled (−)-amino-amide free base (2.6 mmole) to 0.35 g of maleic acid in ethyl acetate at 60° C. The solvent is removed. The residue is triturated with ethyl acetate to obtain 660 mg of the titled maleate salt as a white solid, mp 168°-169° C. A 10 mg portion of this white crystalline solid is dissolved in 1.1 ml of methanol (concentration 9.09 mg/ml) and the $[\alpha]\lambda^{25°}$ C. rotation figures are measured on this solution:

| λ | Hg 578 | 546 | 436 | 365 | Na 589 |
|---|---|---|---|---|---|
| $[\alpha]\lambda^{25°\ C.}$ | −20.5° | −23.6° | −44.2° | −44.2° | −19.5° |

The analytical sample from the 660 mg lot has a C:H:N ratio of 57.33:5.89:5.72. Calculated for $C_{19}H_{24}N_2Cl_2O \cdot C_4H_4O_4$:57.14:5.84:5.97.

A second crop (80 mg) of maleate salt from the mother liquors from the trituration has a melting point of 169°-170° C.

The absolute configuration of the titled (−)-amino-amide is determined by hydrogenation to the known

[1S-(1α,2β)]-(−)-3,4-dichloro-N-methyl-N-[2-(1-pyrrolidinyl)cyclohexyl]benzeneacetamide which can also be named trans-(1)-2-(3,4-dichlorophenyl)-N-methyl-N-[2-(1-pyrrolidinyl)cyclohexyl]acetamide, the compound of Example 35 of Szmuszkovicz U.S. Pat. No. 4,145,435.

Thus a solution of 50 mg of the titled (−)-aminoamide in 25 ml of ethyl acetate is hydrogenated for 1.5 hours at atmospheric pressure over platinum (from 15 mg of platinum oxide). The solution was vigorously magnetically stirred. The platinum was removed by filtering through celite filter aid, and the celite was washed with two 5 ml portions of ethyl acetate. Evaporation of the solvent afforded the known [1S-(1α,2β)-(−)-3,4-dichloro-N-methyl-N-[2-(1A-pyrolidinyl)cyclohexyl]benzeneacetamide. The titled (−)-aminoamide thus has the (1S,2S) absolute configuration.

EXAMPLE 3

[1R-(1α,2β)-(+)-3,4-dichloro-N-[2-(2,5-dihydro-1H-pyrrol-1-yl)-cyclohexyl]-N-methylbenzeneacetamide and its maleate salt A. Resolution of (1α,2β)-(±)-2-(2,5-dihydro-1H-pyrrol-1-yl)-N-methylcyclohexanamine. Preparation of (1α,2β)-(−)-2-(2,5-dihydro-1H-pyrrol-1-yl)-N-methylcyclohexanamine.

1.77 g (9.83 mmole) of the subtitled racemic diamine and 3.97 g (10.3 mmole) of di-p-toluoyl-1-tartaric acid are each separately dissolved in a minimum volume of methanol and the two solutions are mixed together. Crystallization occurs and the solid is filtered and recrystallized from 100 ml of methanol. The resulting solid is partitioned between ethyl acetate and 10% (w/v) sodium hydroxide aqueous solution. The organic layer is washed with brine, dried over anhydrous magnesium sulfate, and concentrated in vacuo to give 0.46 g of the subtitled (−)-diamine. A 54 mg sample of this (−)-diamine is dissolved in 5.0 ml of methanol (concentration 10.8 mg/ml) and the rotation figures are measured as above:

| λ | Hg 578 | 546 | 436 | 365 | Na 589 |
|---|---|---|---|---|---|
| $[\alpha]\lambda^{25°\ C.}$ | −102.6° | −116.2° | −192.9° | −293.2° | −98.5° |

B. [1R-(1α,2β)]-(+)-3,4-dichloro-N-[2-(2,5-dihydro-1H-pyrrol-1-yl)-cyclohexyl]-N-methylbenzeneacetamide, and its maleate salt.

A mixture of 0.73 g (3.6 mmole) of 3,4-dichlorophenylacetic acid, 0.46 g (2.6 mmole) of the (−)-diamine from Part A above and 0.58 g (3.6 mmole) of N,N'-carbonyldiimidazole in 25 ml of methylene chloride is stirred overnight and purified as described in Example 1, Part B above to give 0.57 g of the pure titled (+)-amino-amide product. The maleate salt of this 0.57 g of titled (+)-amino-amide is prepared by reaction with 0.21 g of maleic acid. Upon recrystallizing this maleate salt from ethyl acetate, the first crop (50 mg.) has a melting point of 183°–186° C. A 12 mg. portion of this maleate salt was dissolved in 1 ml of methanol. The $[\alpha]\lambda^{25°\ C.}$ rotations were:

| Hg 578 | 546 | 436 | 365 | Na 589 |
|---|---|---|---|---|
| +8.5° | 9.9° | 18.5° | 34° | 8.2 |

The residue was recrystallized from a 50:50 v/v methylene chloride-diethyl ether mixture to obtain oily crystals which were triturated with diethyl ether to obtain 330 mg of the titled (+)-amino-amide maleate salt as an off-white solid which softened at 123° C. (no clear melting point) and which has the following rotations (11.5 mg/ml in methanol):

| λ | Hg 578 | 546 | 436 | 365 | Na 589 |
|---|---|---|---|---|---|
| $[\alpha]\lambda^{25°\ C.}$ | +19.6° | +22.8° | +43.8° | +82.3 | +18.8 |

EXAMPLE 4

Following the procedure of Example 1, Part G of U.S. Pat. No. 4,360,531, the N-methyl amine compound, 7-methylspiro[7-azabicyclo[4.1.0]heptane-3,2'-[1,3]-dioxolane] is reacted with 2,5-dihydro-1H-pyrrole to form a mixture of the diamines, (7α,8β)-(±)-8-(N-methylamino)-7-(2,5-dihydro-1H-pyrrol-1-yl)-1,4-dioxaspiro[4.5]decane and (7α,8β)-(±)-7-(N-methylamino)-8-(2,5-dihydro-1H-pyrrol-1-yl)-1,4-dioxaspiro[4.5]decane.

This diamine mixture is reacted with 3,4-dichlorophenylacetic acid in the presence of dicyclohexylcarbodiimide in an ether solvent, to form a mixture of (7α,8β)-(±)-3,4-dichloro-N-methyl-N-[7-(2,5-dihydro-1H-pyrrol-1yl)-1,4-dioxaspiro[4.5]dec-8-yl]benzeneacetamide and (7α,8β)-(±)-3,4-dichloro-N-methyl-N-[8-(2,5-dihydro-1H-pyrrol-1-yl)-1,4-dioxaspiro[4.5]dec-7-yl]benzeneacetamide, which are purified by known techniques and procedures.

EXAMPLE 5

(1α,2β,3β)-4-Bromo-N-[3-methoxy-2-(2,5-dihydro-1H-pyrrol-1-yl)-cyclohexyl]-N-methylbenzamide, and its monohydrobromide A. (1α,2β,6β)-2-[[(1,1-dimethylethyl)dimethylsilyl]oxy]-6-(2,5-dihydro-1H-pyrrol-1-yl)cyclohexanol, and (1α,2β,6α)-2-[[(1,1-dimethylethyl)dimethylsilyl]oxy]-6-(2,5-dihydro-1H-pyrrol-1-yl)cyclohexanol A mixture of 4.5 g (19.7 mmol) of pure (1α,2β,6α)-2-[[(1,1-dimethylethyl)dimethylsilyl]oxy]-7-oxabicyclo[4.1.0]heptane, prepared as described in U.S. Pat. No. 4,359,476, Example 1, part A, and 50 ml of 2,5-dihydro-1H-pyrrole is refluxed for 16 hours or until chromatographic analyses of samples of the reaction mixture show none of the above heptane starting material. Unreacted 2,5-dihydro-1H-pyrrole is removed at reduced pressure to leave the above named 6-(2,5-dihydro-1H-pyrrol-1-yl)cyclohexanol intermediate as an oil residue.

This crude oil residue product can be chromatographed, e.g., on 325 g of silica gel eluting initially with an NH₃—MeOH—EtOAc, 0.4:3.6:96 (v/v) mixture and finally with NH₃—MeOH—EtOAc 1:9:90 (v/v) to give the above named pure (1α,2β,6β)- and (1α,2β,6α)-isomers.

Analytical samples of these intermediate compounds can be prepared by treating the named intermediate with ethereal hydrogen bromide or hydrogen chloride to yield the respective hydrobromide or hydrochloride salts.

B. (1α,2α,6β)-1-[2-[[(1,1-dimethylethyl)dimethylsilyl]oxy]-6-(methylamino)cyclohexyl]-2,5-dihydro-1H-pyrrole To an ice cold solution of about 3.4 g of the (1α,2β,6β)-amino alcohol from part A above and 1.94 g (0.0192 mole) of triethylamine in 50 ml of methylene chloride there is added 1.57 g (0.0137 mole) of methanesulfonyl chloride over 30 minutes under a nitrogen atmosphere. If thin layer chromatographic analysis (tlc) of a sample of the reaction mixture indicates incomplete reaction additional methanesulfonyl chloride can be added until the analyses indicate reaction is complete to form the methanesulfonate ester intermediate of the alcohol moiety of the starting amino alcohol. The resulting product mixture is treated with methylene chloride and water which causes two liquid layers to form. The organic liquid phase is separated, dried over magnesium sulfate, and concentrated in vacuo to remove methylene chloride and volatiles. The residue is treated with 20 ml of anhydrous methylamine, placed in a stainless steel bomb and heated to 60° C. for twenty hours. The excess methylamine is evaporated and the residue is distributed between ethyl acetate and water. The organic liquid phase is separated, dried (MgSO4) and concentrated in vacuo to leave the crude sub-titled diamine which can be used without further purification.

C.
(1α,2β,3β)-4-bromo-N-[3-hydroxy-2-(2,5-dihydro-1H-pyrrol-1-yl)-cyclohexyl]-N-methylbenzamide To a stirred solution of 3.04 g of (1α,2α,6β)-1-[2-[[(1,1-dimethylethyl)dimethylsilyl]oxy]-6-(methylamino)cyclohexyl]-2,5-dihydro-1H-pyrrole, from part B above, and 1.17 g (0.0116 mole) of triethylamine in 175 ml of diethyl ether there is added a solution of 2.55 g (0.0116 mole) of 4-bromobenzoyl chloride in 75 ml of diethyl ether over 30 minutes. The mixture is stirred for two hours to ensure complete reaction and filtered. The filtrate is washed with water, 10 percent sodium hydroxide in water solution, water again, saturated sodium chloride in water solution (brine), and then dried (MgSO4) and concentrated in vacuo leaving the hydroxy-protected derivative of the above sub-titled benzamide as crude product.

This crude product intermediate can be further purified by chromatography on 300 g of silica gel eluting with a methanol:ammonium hydroxide:ethyl acetate, 0.9:0.1:99 (v/v) mixture to obtain the hydroxy-protected derivative of the subtitled amino-amide intermediate for further use without further characterization.

A stirred solution of 0.99 g of this hydroxy-protected derivative of the subtitled amino-amide in 10 ml of 7.1N hydrogen chloride in ethanol is heated to 60° for three days. If the analysis indicates incomplete deprotection, HCl gas is bubbled into the solution for one minute to increase the acidity, and the mixture is refluxed for 20 hours. The mixture is concentrated in vacuo and the residue is distributed between 10% NaOH aqueous solution and ethyl acetate. The organic phase is separated, dried (MgSO4) and concentrated in vacuo to afford the crude deprotected subtitled hydroxy-benzamide compound, whih can be further purified.

D. (1α,2β,3β)-4-bromo-N-[3-methoxy-2-(2,5-dihydro-1H-pyrrol-1-yl)cyclohexyl]-N-methylbenzamide, and its monohydrobromide.

A solution of 0.0624 g (0.0026 mole) of sodium hydride (freed from mineral oil by washing with dry tetrahydrofuran) in 10 ml of DMF is treated with 0.50 g of the hydroxybenzamide from part C above at ambient temperature under a nitrogen atmosphere. After 1 hour, 0.37 g (0.0026 mole) of methyl iodide is added and the mixture is stirred overnight. The resulting mixture is distributed beween 400 ml each of water and diethyl ether. The aqueous phase is washed twice with diethyl ether and the combined organic phases are washed with brine solution, dried (MgSO4) and concentrated in vacuo leaving the named-benzamide as an oil. The benxamide oil residue can be treated with a hydrogen bromide in diethyl ether mixture to precipitate the above named hydrobromide salt, which can be recrystallized and further purified from a methanol/ethyl acetate mixture to give the titled compound as its hydrobromide salt.

EXAMPLE 6

(1α,2β)-(±)-4-Bromo-N-[2-(2,5-dihydro-1H-pyrrol-1-yl)cyclohexyl]-N-methylbenxamide Using the method of General Procedure B of U.S. Pat. No. 4,098,904, the diamine from Example 1, Part A above is reacted with 4-bromobenzoyl chloride in diethyl ether in the presence of triethylamine to produce the titled amino-amide which is further purified by known techniques and procedures such as extraction, column chromatography, crystallization and the like.

EXAMPLE 7

(7α,8β)-(±)-4-Bromo-N-[8-(2,5-dihydro-1H-pyrrol-1-yl)-1,4-dioxaspiro[4.5]dec-7-yl]-N-methylbenzamide
and
(7α,8β)-(±)-4-bromo-N-[7-(2,5-dihydro-1H-pyrrol-1-yl)-1,4-dioxaspiro[4.5]dec-8-yl]-N-methylbenzamide Reacting the diamine mixture prepared as described in Example 4 above with 4-bromobenzoyl chloride in diethyl ether in the presence of triethylamine by the method of Example 9 of U.S. Pat. No. 4,360,531 gives a mixture of the titled amino-amides, which are purified by known techniques and procedures.

EXAMPLE 8

(6α,7β)-(±)-3,4-Dichloro-N-[7-(2,5-dihydro-1H-pyrrol-1-yl)-1,4-dioxaspiro[4.5]dec-6-yl]-N-methylbenzeneacetamide The titled compound is prepared using a modification of some of the methodology of Examples 3 and 8 of U.S. Pat. No. 4,359,476 such that hydrogenation conditions are not used.

A. (6α,7β)-(±)-N-[7-(2,5-dihydro-1H-pyrrol-1-yl)]-N-methyl-1,4-dioxaspiro[4.5]decan-6-amine Spiro[1,3-dioxolane]-2,2'-[7-oxabicyclo[4.1.0]heptane] is reacted with methylamine in a pressure vessel at elevated temperature (for example on a steam bath) for a time sufficient to produce (6α,7β)-(±)-7-(methylamino)-1,4-dioxaspiro[4.5]decan-6-ol, which is purified by known techniques and procedures.

This trans amino alcohol is reacted with methanesulfonyl chloride in methylene chloride in the presence of triethylamine to produce the methanesulfonate ester thereof, which is reacted with 2,5-dihydro-1H-pyrrole at elevated temperature (for example up to 100° C.) for a time sufficient to produce the subtitled diamine, which is purified by known techniques and procedures.

B.
(6α,7β)-(±)-3,4-Dichloro-N-[7-(2,5-dihydro-1H-pyrrol-1-yl)-1,4-dioxaspiro[4.5]dec-6-yl]-N-methylbenzeneacetamide The diamine from Part A above is reacted with N,N'-carbonyldiimidazole and 3,4-dichlorophenylacetic acid as described in Example 1, Part B above to give the titled amino-amide which is purified by known techniques and procedures.

EXAMPLE 9

(6α,7β)-(±)-4-Bromo-N-[7-(2,5-dihydro-1H-pyrrol-1-yl)-1,4-dioxaspiro[4.5]dec-6-yl]-N-methylbenzamide The diamine from Example 8, Part A above is reacted with 4-bromobenzoyl chloride in diethyl ether in the presence of triethylamine to produce the titled amino-amide, which is purified by known techniques and procedures.

EXAMPLE 10

(6α,7β)-(±)-3,4-Dichloro-N-[6-(2,5-dihydro-1H-pyrrol-1-yl)-1,4-dioxaspiro[4.5]dec-7-yl]-N-methylbenzeneacetamide A. (6α,7β)-(±)-N-[6-(2,5-dihydro-1H-pyrrol-1-yl)-N-methyl-1,4-dioxaspiro[4.5]decan-7-amine Using the method of Example 8, Part A of U.S. Pat. No. 4,359,476, spiro[1,3-dioxolane]-2,2'-[7-oxabicyclo[4.1.0]heptane] is reacted with 2,5-dihydro-1H-pyrrole for a time sufficient to produce the intermediate (6α,7β)-(±)-7-(2,5-dihydro-1H-pyrrol-1-yl)-1,4-dioxaspiro[4.5]decan-6-ol. This trans amino alcohol is reacted with methane-sulfonyl chloride in methylene chloride in the presence of triethyl-amine to form the methane-sulfonate thereof, which is reacted with methylamine in a pressure vessel to produce the subtitled diamine, which is purified by known techniques and procedures.

B.

(6α,7β)-(±)-3,4-Dichloro-N-[6-(2,5-dihydro-1H-pyrrol-1-yl)-1,4-dioxaspiro[4.5]dec-7-yl]-N-methylbenzeneacetamide The diamine from Part A above is reacted with N,N'-carbonyldiimidazole and 3,4-dichlorophenylacetic acid as described in Example 1, Part B above to give the titled amino-amide which is purified by known techniques and procedures.

EXAMPLE 11

(6α,7β)-(±)-4-Bromo-N-[6-(2,5-dihydro-1H-pyrrol-1-yl)-1,4-dioxaspiro[4.5]dec-7-yl]-N-methylbenzamide The diamine from Example 10, Part A above is reacted with 4-bromobenzoyl chloride in diethyl ether in the presence of triethylamine to produce the titled amino-amide, which is purified by known techniques and procedures.

Following the above procedures the new 2,5-dihydro-1H-pyrrol-1-yl derivatives of compounds described in U.S. Pat. Nos. 4,145,435, 4,098,904, 4,360,531 and 4,359,476 can be prepared by substituting 2,5-dihydro-1H-pyrrole wherever pyrrolidine or other cyclic amine compounds are described. However, procedures involving catalytic hydrogenation cannot be utilized for 2,5-dihydro-1H-pyrrol-1-yl containing compounds because the double bond would be hydrogenated under the conditions employed.

Other reprsentative examples of compounds within the scope of this invention which can be prepared by procedures described in this specification are the cis- and trans-isomers of:

a. 4-methoxy-N-methyl-N-[2-(2,5-dihydro-1H-pyrrol-1-yl)cyclohexyl]benzamide,
b. 3-hydroxy-N-methyl-N-[2-(2,5-dihydro-1H-pyrrol-1-yl)cyclohexyl]benzeneacetamide,
c. 4-azido-N-[4-mercapto-2-(2,5-dihydro-1H-pyrrol-1-yl)cyclohexyl]-N-methylbenzeneacetamide,
d. 2-methyl-N-[4-(methylthio)-2-(2,5-dihydro-1H-pyrrol-1-yl)cyclopentyl]benzamide,
e. N-ethyl-N-[8-(2,5-dihydro-1H-pyrrol-1-yl)-1,5-dioxaspiro[5.6]dodecan-9-yl]-[1,1'-biphenyl]-4-acetamide,
f. 3-methanesulfonyl-N-[9-(2,5-dihydro-1H-pyrrol-1-yl)-3-methyl-1,5-dioxaspiro[5.6]dodec-10-yl]-N-(1-propyl)benzamide,
g. 4-cyano-N-methyl-N-[2-(2,5-dihydro-1-H-pyrrol-1-yl)cyclohexyl]benzeneethanethioamide,
h. 4-amino-N-methyl-N-[7-(2,5-dihydro-1H-pyrrol-1-yl)-1,4-dithiaspiro[4.5]dec-8-yl]benzamide,
i. 3-ethoxycarbonyl-N-ethyl-N-[6-(2,5-dihydro-1H-pyrrol-1-yl)-1,4-oxathiaspiro[4.5]dec-7-yl]benzeneacetamide,
j. N-methyl-N-[2-(2,5-dihydro-1H-pyrrol-1-yl)-4-(thioxo)-cyclohexyl]-4-(propionyloxy)benzamide,
k. 2-(acetylamino)-N-[4-methoxy-2-(2,5-dihydro-1H-pyrrol-1-yl)cyclohexyl]-N-methyllbenzenecarbothioamide,
l. 3-(hydroxysulfonyl)-N-methyl-N-[2-(2,5-dihydro-1H-pyrrol-1-yl)cyclohexyl]benzeneacetamide,
m. 2-formyl-N-[4-(hydroxyimino)-2-(2,5-dihydro-1H-pyrrol-1-yl)-cyclohexyl]-N-methylbenzeneacetamide,
n. N-[5-(acetyloxyimino)-2-(2,5-dihydro-1H-pyrrol-1-yl)cyclohexyl]-N-methyl-4-(2-propen-1-yl)benzamide,
o. 3-benzoyl-N-ethyl-N-[2-(2,5-dihydro-1H-pyrrol-1-yl)cyclopentyl]benzeneacetamide,
p. 3,4-dichloro-N-methyl-N-[8-(2,5-dihydro-1H-pyrrol-1-yl)-3,3-dimethyl-1,5-dithiaspiro[5.5]undec-9-yl]benzeneacetamide,
q. 4-bromo-N-methyl-N-[4-oxo-2-(2,5-dihydro-1H-pyrrol-1-yl)-cyclohexyl]benzamide, and the like, and pharmacologically acceptable salts thereof.

GENERAL CHEMICAL STRUCTURES

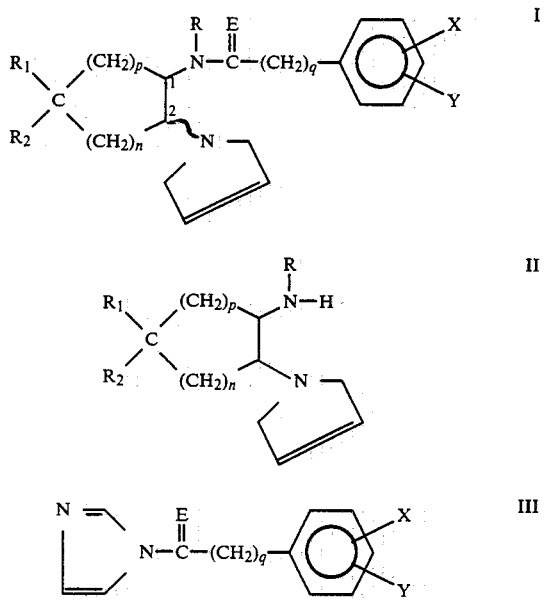

-continued
GENERAL CHEMICAL STRUCTURES

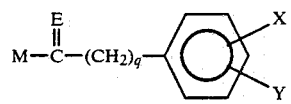   IV

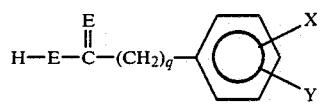   V

We claim:
1. A compound selected from the group consisting of 3,4-dichloro-N-[2-(2,5-dihydro-1H-pyrrol-1-yl)cyclohexyl]-N-methylbenzeneacetamide, isomeric forms of said compound, and 4-trifluoromethyl-N-[2-(2,5-dihydro-1H-pyrrol-1-yl)cyclohexyl]-N-methylbenzamide, or a pharmaceutically acceptable salt of any of the above compounds.
2. A compound according to claim 1 wherein the compound is 3,4-dichloro-N-[2-(2,5-dihydro-1H-pyrrol-1-yl)cyclohexyl]-N-methylbenzeneacetamide, or a pharmacologically acceptable salt thereof.
3. A compound according to claim 1 wherein the compound is (+)-3,4-dichloro-N-[2-(2,5-dihydro-1H-pyrrol-1-yl)cyclohexyl]-N-methylbenzeneacetamide, or a pharmacologically acceptable salt thereof.
4. A compound according to claim 1 wherein the compound is (1α,2β)-(+)-3,4-dichloro-N-[2-(2,5-dihydro-1H-pyrrol-1-yl)cyclohexyl]-N-methylbenzeneacetamide, or a pharmacologically acceptable salt thereof.
5. A compound according to claim 1 wherein the compound is (−)-3,4-dichloro-N-[2-(2,5-dihydro-1H-pyrrol-1-yl)cyclohexyl]-N-methylbenzeneacetamide, or a pharmacologically acceptable salt thereof.
6. A compound according to claim 1 wherein the compound is (1α,2β)-(−)-3,4-dichloro-N-[2,5-dihydro-1H-pyrrol-1-yl)cyclohexyl]-N-methylbenzeneacetamide, or a pharmacologically acceptable salt thereof.
7. A compound according to claim 1 wherein the compound is N-methyl-N-[2-(2,5-dihydro-1H-pyrrol-1-yl)cyclohexyl]-4-trifluoromethylbenzamide, as its methanesulfonate salt.
8. A composition useful in pharmaceutically effective dosage unit form for alleviating pain in warm blooded mammals which comprises a compound of claim 1 in combination with a pharmaceutically acceptable carrier.
9. A method for alleviating pain which comprises administering to an animal suffering pain an analgesically effective amount of a compound of claim 1 in a pharmaceutical dosage unit form.
10. A composition of claim 8 wherein the pain alleviating compound contains (−)(1α,2β)-3,4-dichloro-N-[2-(2,5-dihydro-1H-pyrrol-1-yl)cyclohexyl]-N-methylbenzeneacetamide, or a pharmacologically acceptable salt thereof.
11. A method of claim 9 wherein the analgesically effective compound is (1α,2β)-(−)-3,4-dichloro-N-[2-(2,5-dihydro-1H-pyrrol-1-yl)cyclohexyl]-N-methylbenzeneacetamide, or a pharmacologically acceptable salt thereof.

* * * * *